(12) United States Patent
Skotnicki

(10) Patent No.: US 7,605,258 B2
(45) Date of Patent: Oct. 20, 2009

(54) PROCESSES FOR THE SYNTHESIS OF INDIVIDUAL ISOMERS OF MONO-PEG CCI-779

(75) Inventor: Jerauld Stanley Skotnicki, Westfield, NJ (US)

(73) Assignee: Wyeth, Madison, NJ (US)

( * ) Notice: Subject to any disclaimer, the term of this patent is extended or adjusted under 35 U.S.C. 154(b) by 92 days.

(21) Appl. No.: 11/974,831

(22) Filed: Oct. 16, 2007

(65) Prior Publication Data

US 2008/0097093 A1   Apr. 24, 2008

Related U.S. Application Data

(60) Provisional application No. 60/852,543, filed on Oct. 18, 2006.

(51) Int. Cl.
*C07D 498/18*   (2006.01)
*A61K 31/436*   (2006.01)
*A61P 37/06*   (2006.01)

(52) U.S. Cl. .................................... 540/456
(58) Field of Classification Search .................. 540/456
See application file for complete search history.

(56) References Cited

U.S. PATENT DOCUMENTS

| | | | |
|---|---|---|---|
| 5,362,718 | A | 11/1994 | Skotnicki et al. |
| 5,780,462 | A | 7/1998 | Lee et al. |
| 5,955,457 | A | 9/1999 | Lee et al. |
| 6,277,983 | B1 | 8/2001 | Shaw et al. |
| 6,432,973 | B1 | 8/2002 | Zhu et al. |
| 7,074,804 | B2 | 7/2006 | Zhu et al. |
| 7,153,957 | B2 | 12/2006 | Chew et al. |
| 7,273,874 | B2 | 9/2007 | Graziani et al. |
| 7,276,498 | B2 | 10/2007 | Graziani et al. |
| 2005/0033046 | A1 | 2/2005 | Chew et al. |
| 2006/0036091 | A1 | 2/2006 | Cai et al. |
| 2006/0178392 | A1 | 8/2006 | Deshmukh et al. |
| 2007/0129541 | A1 | 6/2007 | Zhang et al. |

FOREIGN PATENT DOCUMENTS

| | | |
|---|---|---|
| WO | WO-02/24706 | 3/2002 |
| WO | WO-2007/103348 | 9/2007 |

*Primary Examiner*—Bruck Kifle
(74) *Attorney, Agent, or Firm*—David A. Rubin, Esq.; Howson & Howson LLP

(57) ABSTRACT

Processes for preparing individual diastereomers of mono-pegylated rapamycin 42 ester with 3-hydroxy-2-(hydroxymethyl)-2-methylpropionic acid (CCI-779) are provided.

25 Claims, No Drawings

PROCESSES FOR THE SYNTHESIS OF INDIVIDUAL ISOMERS OF MONO-PEG CCI-779

CROSS-REFERENCE TO RELATED APPLICATIONS

This application claims the benefit of the priority of U.S. Provisional Patent Application No. 60/852,543, filed Oct. 18, 2006.

BACKGROUND OF THE INVENTION

Rapamycin 42-ester with 3-hydroxy-2-(hydroxymethyl)-2-methylpropionic acid (CCI-779, temsirolimus) has demonstrated significant inhibitory effects on tumor growth in both in vitro and in vivo models. CCI-779 binds to and forms a complex with the cytoplasmic protein FKBP, which inhibits an enzyme, mTOR (mammalian target of rapamycin, also known as FKBP12-rapamycin associated protein [FRAP]). Inhibition of mTOR's kinase activity inhibits a variety of signal transduction pathways, including cytokine-stimulated cell proliferation, translation of mRNAs for several key proteins that regulate the G1 phase of the cell cycle, and IL-2-induced transcription, leading to inhibition of progression of the cell cycle from G1 to S. CCI-779 has been demonstrated to be effective in multiple applications, including but not limited to inhibition of central nervous system cancer, leukemia, breast cancer, prostate cancer, melanoma, gliomas, and glioblastoma.

Polyethylene glycol (PEG) is a linear or branched, neutral polymer available in a variety of molecular weights and is soluble in water and most organic solvents. The preparation and use of pegylated rapamycin derivatives has been described in U.S. Pat. Nos. 5,955,457 and 6,432,973. In the processes described therein, hydroxyesters of rapamycin (prepared as described in the literature, e.g., U.S. Pat. Nos. 5,362,718 and 6,277,983, and U.S. Patent Publication No. US 2005-0033046 A1) are acylated and the resulting compound is reacted with a polyethylene glycol.

Use of the processes to prepare mono-pegylated CCI-779 yields a pair of stereoisomers. Such stereoisomers require further separation steps are required to obtain a single isomer of mono-pegylated CCI-779, which is difficult and costly. What is needed are processes enabling the preparation of a readily separated isomer of mono-pegylated CCI-779.

SUMMARY OF THE INVENTION

In one embodiment, a process is provided for preparing an individual isomer of mono-pegylated rapamycin 42 ester with 3-hydroxy-2-(hydroxymethyl)-2-methylpropionic acid (CCI-779) by pegylating

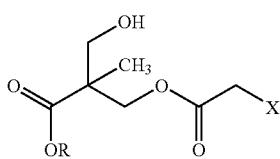

with HY—(CH$_2$CH$_2$O)$_n$CH$_3$, resolving the isomers thereof, and reacting an individual isomer with rapamycin.

In a further embodiment, a process is provided for preparing an individual isomer of mono-pegylated rapamycin 42 ester with 3-hydroxy-2-(hydroxymethyl)-2-methylpropionic acid (CCI-779) by reacting

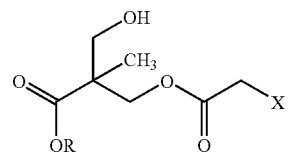

with HY—(CH$_2$CH$_2$O)$_n$CH$_3$, wherein X, Y, R, and n are defined herein; (b) protecting the alcohol group of the product of (a); (c) deprotecting the acid of the product of (a); (d) resolving the isomers of (c); (e) reacting an individual isomer of (d) with rapamycin; and (f) deprotecting the product of (e).

In another embodiment, a process is provided for preparing an individual isomer of mono-pegylated CCI-779 by resolving the isomers of

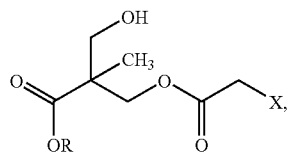

reacting an individual isomer with rapamycin, and pegylating the individual CCI-779 isomer with HY—(CH$_2$CH$_2$O)$_n$CH$_3$.

In still a further embodiment, a process is provided for preparing an individual isomer of mono-pegylated rapamycin 42 ester with 3-hydroxy-2-(hydroxymethyl)-2-methylpropionic acid (CCI-779) by (a) resolving the isomers of

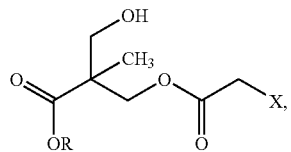

wherein X and R are defined herein; (b) protecting the alcohol group of an isomer product of (a); (c) deprotecting the acid of an isomer product of (b); (d) reacting the product of (c) with rapamycin; (e) reacting the product of (d) with HY—(CH$_2$CH$_2$O)$_n$CH$_3$, wherein Y and n are defined herein; and (f) deprotecting the product of (e).

Other aspects and advantages of the invention will be readily apparent from the following detailed description of the invention.

DETAILED DESCRIPTION OF THE INVENTION

Provided herein are processes for the preparation of an individual isomer of mono-pegylated rapamycin 42-ester with 3-hydroxy-2-(hydroxymethyl)-2-methylpropionic acid (CCI-779).

Mono-pegylated CCI-779 has the following structure:

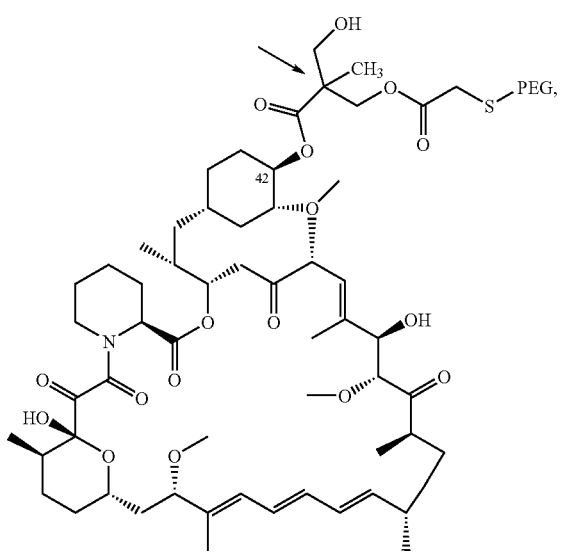

wherein PEG represents a polyethylene glycol as defined herein. The 42-substituent has a single chiral center (identified by an arrow in the above structure), which provides two diastereomers of mono-pegylated CCI-779. Unless otherwise indicated, the term "isomer" is used herein to refer to such a diastereomer. These two isomers ("A" and "B") have the following formulae:

Isomer A

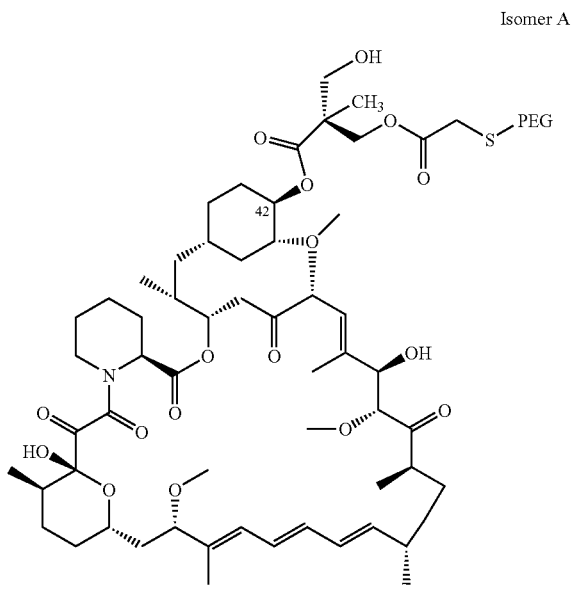

-continued

Isomer B

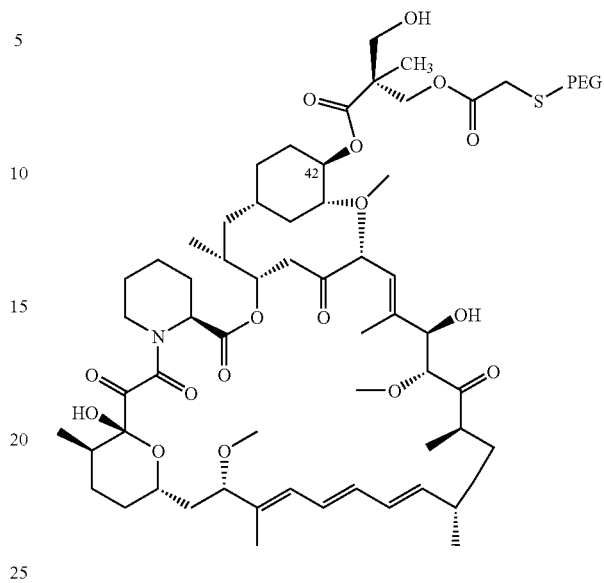

The terms "polyethylene glycol", "PEG" and "nPEG", as used herein, refer to a substituent having structure —$(CH_2CH_2O)_nCH_3$. In one embodiment, n is an integer from 5 to 450. In other embodiments, n is 5 to 200, 8 to 20, or 90 to 120. In still another embodiment, n is 8 to 135. The term "pegylation" or "mono-pegylation" is referred to herein to describe the attachment of a single Y—$(CH_2CH_2O)_nCH_3$ group to the 42-ester of the rapamycin through the Y atom, wherein n is as defined herein. In one embodiment, Y is S (sulfur). In another embodiment, Y is O (oxygen). In one embodiment, nPEG-SH is utilized, wherein "n" is as defined above. Polyethylene glycol of varying lengths may be obtained commercially or prepared by conventional techniques.

In one embodiment, mono-acylated 2,2-bis-hydroxymethyl-2-propanoic acid as used in the processes described herein is obtained as a mixture of enantiomers by reacting an acetic acid of the formula X—$CH_2CO_2H$ with 2,2-bis-hydroxymethyl-2-propanoic acid (acid protected) in the presence of a coupling agent and a base catalyst, wherein X is a leaving group and R is a protecting group as described herein. In one embodiment, the acetic acid is 2-iodoacetic acid.

In other embodiments, an enantiomeric mixture of mono-acylated 2,2-bis-hydroxymethyl-2-propanoic acid is obtained commercially or prepared by other techniques known in the art. The source of mono-acylated 2,2-bis-hydroxymethyl-2-propanoic acid is not a limitation of the embodiments described herein, and it may be generated with or without protection of the acid group, i.e., with or without "R".

In one embodiment, the coupling agent is dicyclohexylcarbodiimide (DCC). In other embodiments, the coupling agent is di-p-dimethylaminophenylcarbodiimide, N,N'-carbonyldiimidazole, benzotriazole, n-ethyl-5-phenylisoxazolene-3'-sulfonate, or diethylcyanophosphate. In another embodiment, the base catalyst is dimethylaminopyridine (DMAP). In other embodiments, the base catalyst is pyridine, triethylamine, or N,N-diisopropylethylamine. In yet another embodiment, the coupling agent dicyclohexylcarbodiimide (DCC) is used in conjunction with the base catalyst dimethylaminopyridine (DMAP). However, the invention is not so limited. Other suitable coupling agents and base catalysts, and combinations thereof, may be selected by one of skill in the art and utilized.

In one embodiment, the leaving group (X) is bromine. In another embodiment, the leaving group (X) is iodine. However, other suitable leaving groups may be selected by one of skill in the art and may be utilized herein.

same or different. As used herein, "Me" represents methyl, "Et" represents ethyl, and "Bu" represents butyl. Other suitable protecting groups may be selected by one of skill in the art and may be Utilized herein.

In one embodiment, an individual isomer of mono-pegylated rapamycin 42 ester with 3-hydroxy-2-(hydroxymethyl)-2-methylpropionic acid (CCI-779) is prepared by the process illustrated in Scheme 1, below.

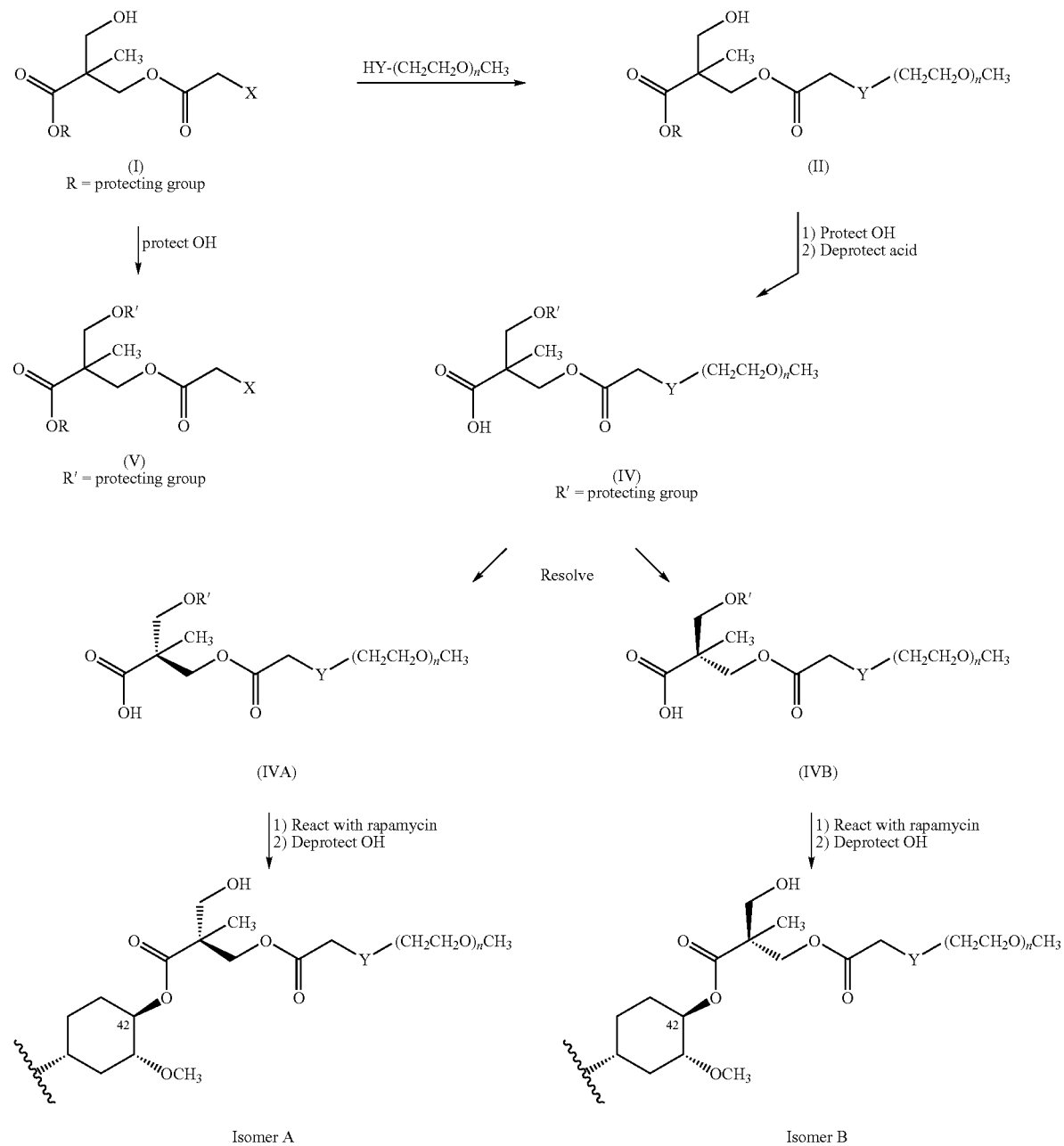

In one embodiment, a protecting group (R or R') is individually selected from amongst benzyl, t-butyl, methyl, $SiMe_3$, $SiEt_3$, or $SiMe_2t$-Bu. By individually, it is meant that in any embodiment, the protecting groups R and R' may be the In another embodiment, an individual isomer of mono-pegylated rapamycin 42 ester with 3-hydroxy-2-(hydroxymethyl)-2-methylpropionic acid (CCI-779) is prepared by the process illustrated in Scheme 2, below.

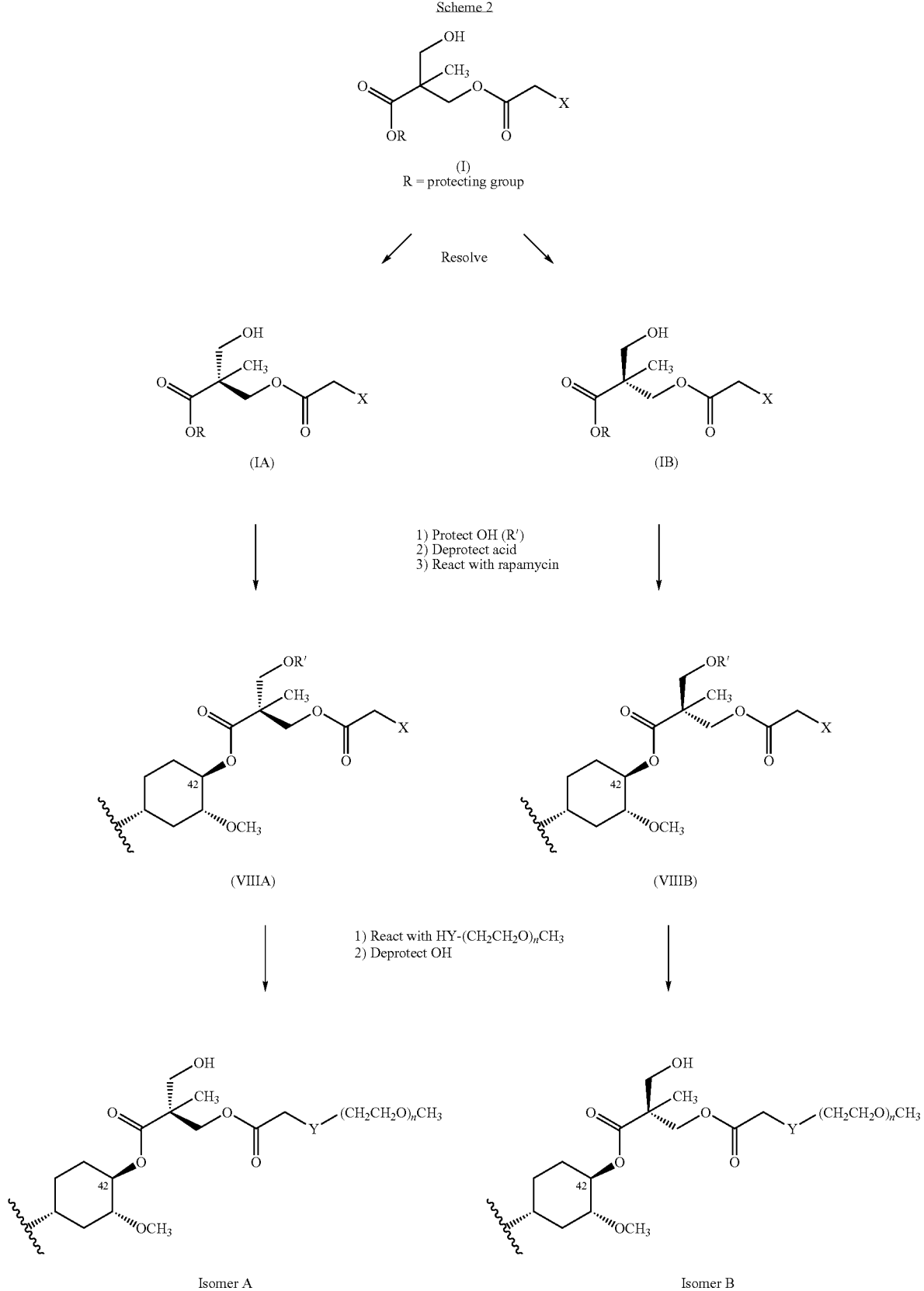

In one embodiment, the pegylation step referred to in the process illustrated in Scheme 1, is accomplished by reacting

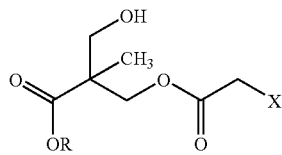

(I), with HY—(CH$_2$CH$_2$O)$_n$CH$_3$. In one example, the following protected, pegylated acid (II) is formed, wherein R, Y, and n are defined above.

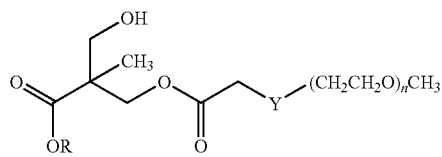

(II)

The —OH group of the pegylated acid (II) may then protected with an R' group using techniques and reagents known to those skilled in the art, as described above, to form compound (III) of the following structure, where R, R', Y, and n are defined above.

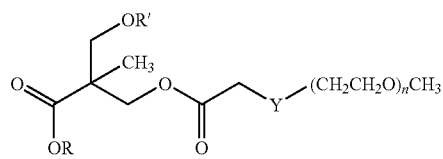

(III)

Compound (III) may then be deprotected at the acid position using techniques and reagents known to those of skill in the art to form a pegylated acid (IV) of the following structure, wherein Y, R', and n are defined above.

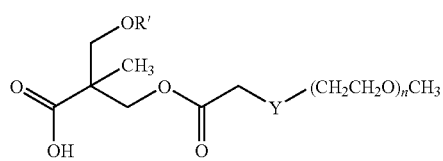

(IV)

In another embodiment, the —OH group of compound (I) may be first protected with protecting group R' as described herein. In one example, the following protected acid (V) is formed, where R, R', and X are defined above.

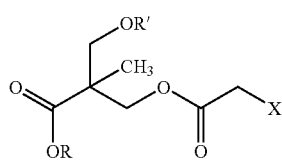

(V)

Compound (V) may then be reacted with HY—(CH$_2$CH$_2$O)$_n$CH$_3$ to form compound (IV) using the procedure described above for pegylating compound (I).

In another embodiment, a pegylation step as referred to in the process illustrated in Scheme 1, is accomplished by reacting individually

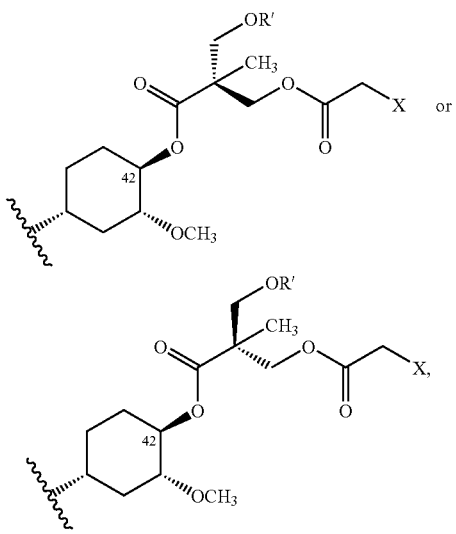

with HY—(CH$_2$CH$_2$O)$_n$CH$_3$.

In one embodiment, isomers obtained by the processes described herein and illustrated in Schemes 1 and 2 above may be resolved into individual enantiomers by reacting the isomers with a chiral amine. In a further embodiment, the chiral amine is (+)PhCHMeNH$_2$ or (−)PhCHMeNH$_2$. As used herein, "Ph" represents a phenyl group. The resulting diastereomers may thereafter be separated by conventional means. In one embodiment, the diastereomers are separated by crystallization or chromatography, either alone or in any order. In another embodiment, both crystallization and chromatography are utilized.

In another embodiment, isomers obtained by the processes described herein and illustrated in Schemes 1 and 2 above may be resolved into individual enantiomers by reacting the isomers with a chiral alcohol. In a further embodiment, the chiral alcohol is (+)PhCHMeOH or (−)PhCHMeOH, (+)menthol, or (−)menthol. The resulting diastereomers may thereafter be separated by conventional means. In one embodiment, the diastereomers are separated by crystallization, chromatography, or distillation, either alone or in combination in any order. In another embodiment, crystallization is employed. In yet another embodiment, chromatography is employed. In still another embodiment, distillation is employed.

Resolution of pegylated acid (IV) results in the production of the following isomers (IVA) and (IVB):

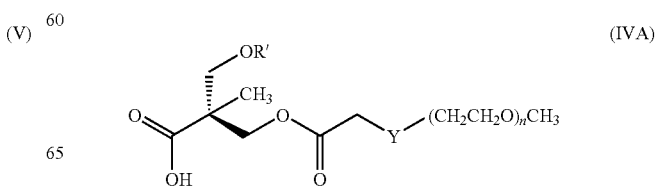

(IVA)

-continued

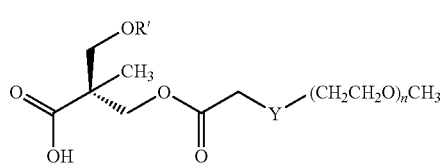 (IVB)

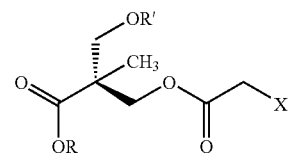 (VIA)

Compounds (IVA) and (IVB) may then be independently reacted with rapamycin using techniques known in the art to form compounds (XA) and (XB), wherein R', Y, and n are defined herein and the wavy line represents the remaining backbone of the rapamycin molecule.

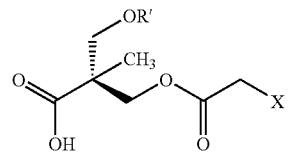 (VIB)

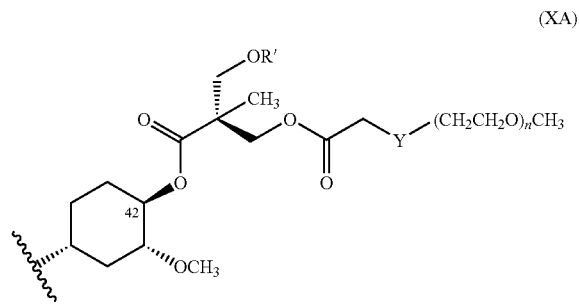 (XA)

The OR group of the acid moiety of compounds (VIA) and (VIB) may then be independently deprotected using techniques and reagents known to those skilled in the art to form compounds (VIIA) and (VIIB), wherein R' and X defined above.

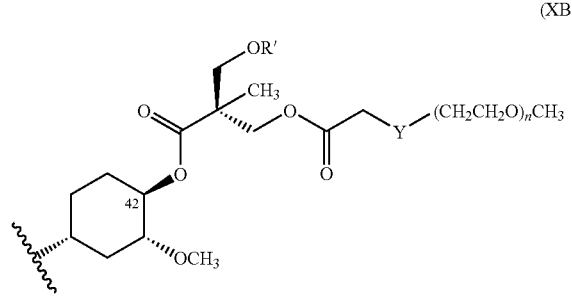 (XB)

(VIIA)

(VIIB)

Independent deprotection of the OR' group of compounds (XA) and (XB) using techniques and reagents known in the art provides Isomers A and B.

Similarly, resolution of compound (I) provides the following isomers (IA) and (IB), wherein R and X are defined above.

Once deprotected, acid compounds (VIIA) and (VIIB) may be independently reacted with rapamycin using techniques and reagents known to those of skill in the art. In one embodiment, compounds (VIIA) and (VIIB) react with rapamycin at the 42-position to form compounds (VIIIA) and (VIIIB), wherein R' and X are defined above and the wavy line represents the remaining backbone of the rapamycin molecule.

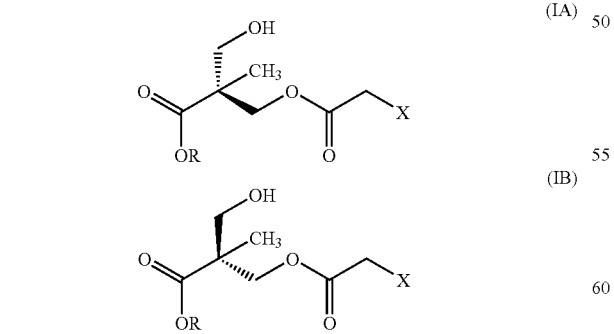

(IA)

(IB)

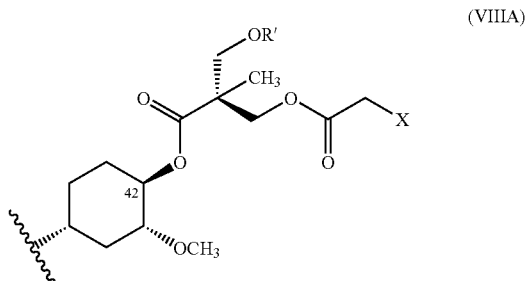 (VIIIA)

The —OH groups of isomers (IA) and (IB) may then independently protected with a R' protecting group as described above to independently form isomers (VIA) and (VIB), wherein R, R', and X are defined above.

-continued (VIIIB)

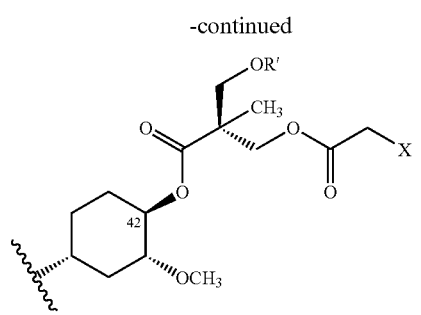

Compounds (VIIIA) and (VIIIB) may then independently be reacted with HY—(CH$_2$CH$_2$O)$_n$CH$_3$ using the techniques described above for the pegylation of compound (I) to form compounds (IXA) and (IXB) of the following structure:

(IXA)

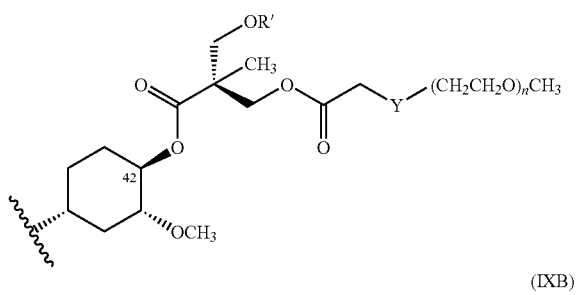

(IXB)

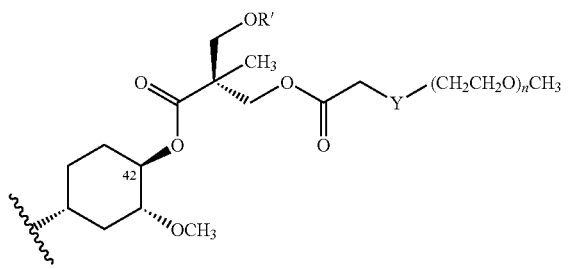

The OR' group of compounds (IXA) and (IXB) may then be independently deprotected using techniques and reagents known of skill in the art to prepare Isomers A and B.

Individual isomers of mono-pegylated CCI-779 may be used, alone or in a composition or kit, as an antineoplastic agent, and in particular, in treatment of solid tumors, including sarcomas and carcinomas, astrocytomas, prostate cancer, breast cancer, colon cancer, small cell lung cancer, ovarian cancer, and adult T-cell leukemia/lymphoma.

Individual isomers of mono-pegylated CCI-779 are also useful in the treatment or inhibition of transplantation rejection such as kidney, heart, liver, lung, bone marrow, pancreas (islet cells), cornea, small bowel, skin allografts, and heart valve xenografts; in the treatment or inhibition of graft vs. host disease; in the treatment or inhibition of autoimmune diseases such as lupus including systemic lupus erythematosus, rheumatoid arthritis, diabetes mellitus, myasthenia gravis, and multiple sclerosis; and diseases of inflammation such as psoriasis, dermatitis, eczema, seborrhea, bowel disorders including inflammatory bowel disease, pulmonary inflammation (including asthma, chronic obstructive pulmonary disease, emphysema, acute respiratory distress syndrome, bronchitis, and the like), cardiac inflammatory disease, and ocular inflammation such as ocular uveitis; anemia; adult T-cell leukemia/lymphoma; fungal infections; malignant carcinomas; hyperproliferative vascular diseases such as restenosis; graft vascular atherosclerosis; and cardiovascular disease, cerebral vascular disease, and peripheral vascular disease, such as coronary artery disease, cereberovascular disease, arteriosclerosis, atherosclerosis, nonatheromatous arteriosclerosis, vascular wall damage from cellular events leading toward immune mediated vascular damage, smooth muscle cell proliferation and intimal thickening following vascular injury, and inhibiting stroke or multiinfarct dementia.

All publications listed in this specification are incorporated herein by reference. While the invention has been described with reference to specific embodiments, it will be appreciated that modifications can be made without departing from the spirit of the invention. Such modifications are intended to fall within the scope of the appended claims.

What is claimed is:

1. A process for preparing an individual isomer of mono-pegylated rapamycin 42 ester with 3-hydroxy-2-(hydroxymethyl)-2-methylpropionic acid (CCI-779), said process comprising:

(a) reacting

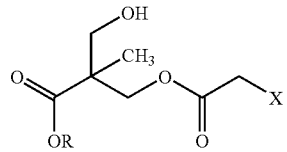

with HY—(CH$_2$CH$_2$O)$_n$CH$_3$,
wherein:
X is a leaving group,
Y is S or O,
R is a protecting group, and
n is an integer from 5 to 450;

(b) protecting the alcohol group of the product of (a);
(c) deprotecting the acid group of the product of (b);
(d) resolving the isomers of (c) using a chiral amine or a chiral alcohol;
(e) reacting one resolved isomer of (d) with rapamycin; and
(f) deprotecting the product of (e).

2. The process according to claim 1, wherein

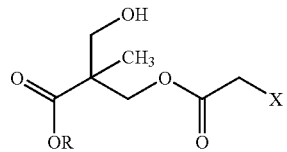

is obtained by reacting X—CH$_2$CO$_2$H with

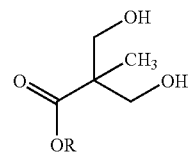

in the presence of a coupling agent and a base catalyst.

3. The process according to claim 2, wherein the coupling agent is dicyclohexylcarbodiimide (DCC).

4. The process according to claim 2, wherein the base catalyst is dimethylaminopyridine (DMAP).

5. The process according to claim 1, wherein X is iodine.

6. The process according to claim 1, wherein R is selected from the group consisting of benzyl, t-butyl, methyl, SiMe$_3$, SiEt$_3$, and SiMe$_2$t-Bu.

7. The process according to claim 1, wherein Y is S.

8. The process according to claim 1, wherein n is 8 to 135.

9. The process according to claim 1, wherein the isomers of step (c) are resolved in step (d) by reacting the isomers with a chiral amine.

10. The process according to claim 9, wherein the chiral amine is +PhCHMeNH$_2$ or −PhCHMeNH$_2$.

11. The process according to claim 1, wherein the isomers of step (c) are resolved in step (d) by reacting the isomers with a chiral alcohol.

12. The process according to claim 11, wherein the chiral alcohol is +PhCHMeOH, −PhCHMeOH, +menthol, or −menthol.

13. The process according to claim 1, wherein the diastereomers are separated by crystallization, chromatography, or distillation.

14. A process for preparing an individual isomer of monopegylated rapamycin 42 ester with 3-hydroxy-2-(hydroxymethyl)-2-methylpropionic acid (CCI-779), said process comprising:

(a) resolving the isomers of

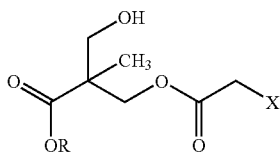

using a chiral amine or a chiral alcohol, wherein X is a leaving group and R is a protecting group;
(b) protecting the alcohol group of an isomer product of (a);
(c) deprotecting the acid group of an isomer product of (b);
(d) reacting the product of (c) with rapamycin;
(e) reacting the product of (d) with HY—(CH$_2$CH$_2$O)$_n$CH$_3$, wherein:
    Y is S or O, and
    n is an integer from 5 to 450; and
(f) deprotecting the product of (e).

15. The process according to claim 14, wherein

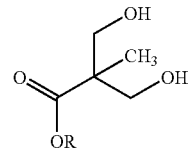

obtained by reacting X—CH$_2$CO$_2$H with

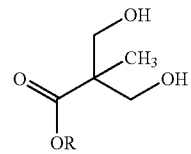

in the presence of a coupling agent and a base catalyst.

16. The process according to claim 15, wherein the coupling agent is dicyclohexylcarbodiimide (DCC).

17. The process according to claim 15, wherein the base catalyst is dimethylaminopyridine (DMAP).

18. The process according to claim 14, wherein X is iodine.

19. The process according to claim 14, wherein R is selected from the group consisting of benzyl, t-butyl, methyl, SiMe$_3$, SiEt$_3$, and SiMe$_2$t-Bu.

20. The process according to claim 14, wherein Y is S.

21. The process according to claim 14, wherein n is 8 to 135.

22. The process according to claim 14, wherein the isomers are resolved in step (a) by reacting the isomers with a chiral amine.

23. The process according to claim 22, wherein the chiral amine is +PhCHMeNH$_2$ or −PhCHMeNH$_2$.

24. The process according to claim 14, wherein the isomers are resolved in step (a) by reacting the isomers with a chiral alcohol.

25. The process according to claim 24, wherein the chiral alcohol is +PhCHMeOH, −PhCHMeOH, +menthol, or −menthol.

* * * * *

UNITED STATES PATENT AND TRADEMARK OFFICE
CERTIFICATE OF CORRECTION

PATENT NO. : 7,605,258 B2  Page 1 of 1
APPLICATION NO. : 11/974831
DATED : October 20, 2009
INVENTOR(S) : Skotnicki It is certified that error appears in the above-identified patent and that said Letters Patent is hereby corrected as shown below:

Col. 16;
Claim 15, replace the following structure spanning lines 6-13:

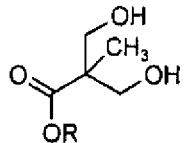

with the following structure:

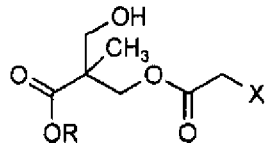

Signed and Sealed this

Twenty-second Day of December, 2009

David J. Kappos
*Director of the United States Patent and Trademark Office*